(12) United States Patent
Muldoon et al.

(10) Patent No.: US 11,779,744 B2
(45) Date of Patent: Oct. 10, 2023

(54) HEMOSTASIS VALVE ASSEMBLY AND METHOD FOR ASSEMBLING A HEMOSTASIS VALVE

(71) Applicant: Creganna Unlimited Company, Galway (IE)

(72) Inventors: Damian Muldoon, Galway (IE); Brian F. Murphy, Galway (IE); Shane Ward, Galway (IE); Liam Ruddy, Galway (IE)

(73) Assignee: Creganna Unlimited Company, Galway (IE)

( * ) Notice: Subject to any disclaimer, the term of this patent is extended or adjusted under 35 U.S.C. 154(b) by 527 days.

(21) Appl. No.: 17/001,504

(22) Filed: Aug. 24, 2020

(65) Prior Publication Data

US 2021/0052877 A1 Feb. 25, 2021

(30) Foreign Application Priority Data

Aug. 23, 2019 (EP) ..................................... 19193408

(51) Int. Cl.
*A61M 39/06* (2006.01)
*B33Y 80/00* (2015.01)

(52) U.S. Cl.
CPC ... *A61M 39/0606* (2013.01); *A61M 2039/062* (2013.01); *A61M 2039/064* (2013.01); *A61M 2207/10* (2013.01); *B33Y 80/00* (2014.12)

(58) Field of Classification Search
CPC ........ A61M 39/0606; A61M 2039/062; A61M 2039/064; A61M 2207/10; A61M 2039/0653; A61M 2039/0686; A61M 39/06; B33Y 80/00
See application file for complete search history.

(56) References Cited

U.S. PATENT DOCUMENTS

| 4,798,594 | A | | 1/1989 | Hilistead |
| 4,857,062 | A | | 8/1989 | Russell |
| 4,929,235 | A | * | 5/1990 | Merry ............... A61M 39/0606 604/167.04 |

(Continued)

FOREIGN PATENT DOCUMENTS

| EP | 0875262 A2 | 11/1998 |
| EP | 0875262 B1 | 1/2002 |

(Continued)

OTHER PUBLICATIONS

Extended European Search Report, dated Nov. 11, 2019, 8 pages.

(Continued)

*Primary Examiner* — Amber R Stiles
(74) *Attorney, Agent, or Firm* — Barley Snyder

(57) ABSTRACT

A hemostasis valve assembly includes a hollow body delimiting an inner passage for inserting a medical material, the inner passage extending between a proximal opening and a distal opening of the hollow body, a distal seal arranged at the distal opening, a proximal seal arranged at the proximal opening, a spacer element arranged between the distal seal and the proximal seal, and an end cap. The distal seal is an elastic valve that is sealed when idle. The end cap has a fixing element engaging a support element of the hollow body to fix a stacked assembly including the distal seal, the spacer element, and the proximal seal inside the hollow body.

18 Claims, 4 Drawing Sheets

(56) References Cited

U.S. PATENT DOCUMENTS

| | | | |
|---|---|---|---|
| 5,009,391 A | | 4/1991 | Steigerwald |
| 5,167,637 A | | 12/1992 | Okada et al. |
| 5,324,271 A | | 6/1994 | Abiuso et al. |
| 5,409,463 A | * | 4/1995 | Thomas ............ A61M 25/0662 |
| | | | 604/167.04 |
| 5,520,643 A | * | 5/1996 | Ensminger ........ A61M 39/0208 |
| | | | 604/245 |
| 5,643,227 A | | 7/1997 | Stevens |
| 9,398,923 B2 | | 7/2016 | Alonso et al. |
| 10,143,828 B2 | | 12/2018 | Furnish et al. |
| 2004/0230161 A1 | | 11/2004 | Zeiner |
| 2010/0179480 A1 | | 7/2010 | Sugiki et al. |
| 2014/0207083 A1 | | 7/2014 | Pessin |
| 2016/0331935 A1 | * | 11/2016 | Saatchi ............. A61M 25/0606 |

FOREIGN PATENT DOCUMENTS

| | | |
|---|---|---|
| WO | 9945996 A1 | 9/1999 |
| WO | 0117587 A1 | 3/2001 |
| WO | 2010087943 A1 | 8/2010 |

OTHER PUBLICATIONS

Examination Report from the European Patent Office dated Nov. 16, 2022, corresponding to Application No. 19 193 408.2-1005, 4 pages.

* cited by examiner

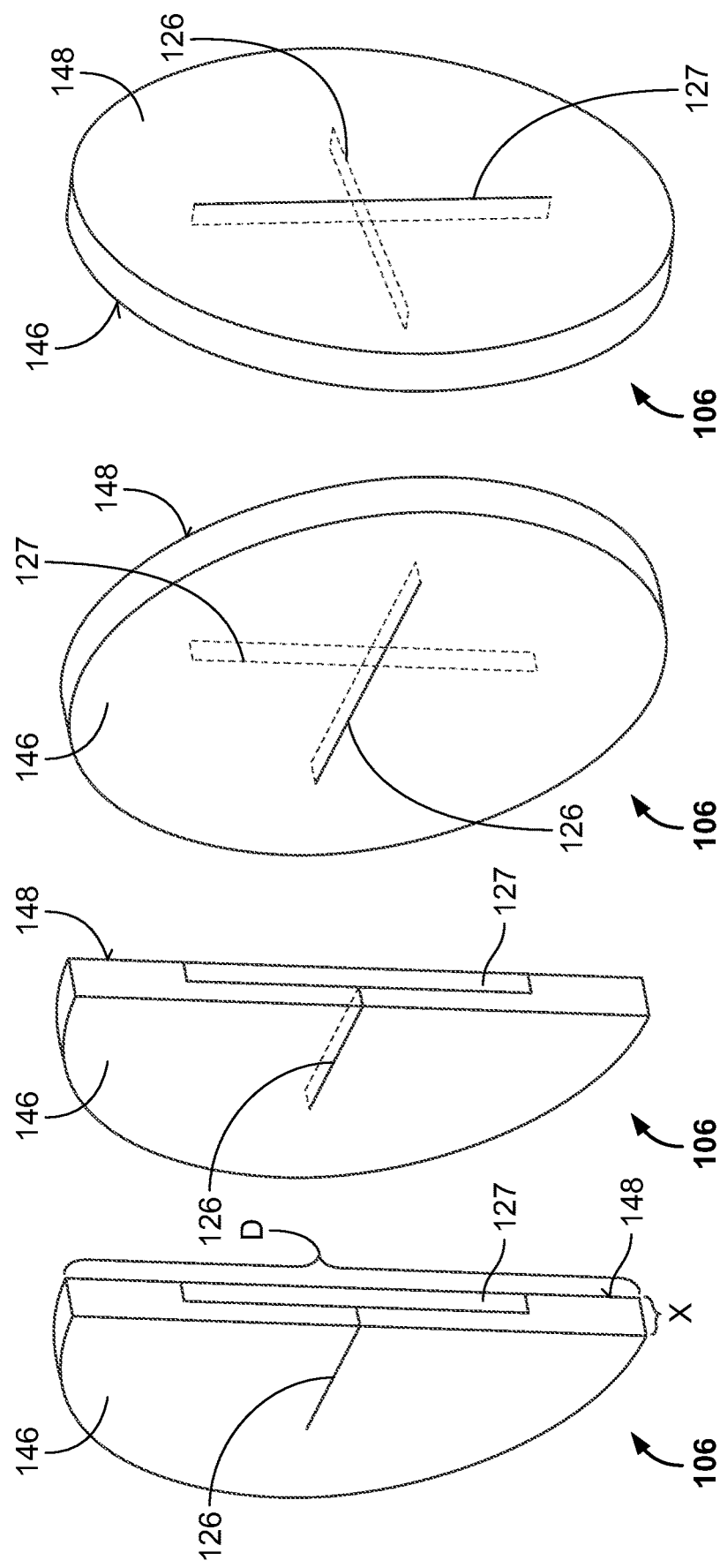

HEMOSTASIS VALVE ASSEMBLY AND METHOD FOR ASSEMBLING A HEMOSTASIS VALVE

CROSS-REFERENCE TO RELATED APPLICATION

This application claims the benefit of the filing date under 35 U.S.C. § 119(a)-(d) of European Patent Application No. 19193408, filed on Aug. 23, 2019.

FIELD OF THE INVENTION

The present invention relates to a valve assembly and, more particularly to a hemostasis valve assembly.

BACKGROUND

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure in which an artificial valve or valve repair device is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more deflecting mechanisms, which can be achieved by a tension cable, or other mechanisms positioned inside the catheter.

However, when performing interventional cardiology, it is necessary to provide blood sealing during the insertion of medical material into the body of a patient. The medical material is for example a catheter, a guide wire, a sheath containing a valve or stent, or the like. To prevent leaks of bodily fluids, in particular blood, during the insertion of the material, it is known to use a hemostasis valve assembly at the insertion point into the patient. Such a hemostasis valve assembly comprises at least one valve for performing a sealing function around the inserted material and for being closed when idle.

Existing hemostasis valve assemblies, however, have the problem that each design is usable only with a small range of diameters of medical material. They also have the problem that for comparatively large diameters (e. g. 34 Fr, i. e. 11.3 mm) no cost efficient off the shelf solutions exist. Presently, the largest Fr size hemostasis valve assembly available as regular off the shelf component is 17 Fr (i. e. 5.7 mm). However, transcatheter aortic valve implantation (TAVI), transaortic mitral valve replacement (TAMVR), and other cardiological therapies require hemostasis valve arrangements with larger inner diameters.

SUMMARY

A hemostasis valve assembly includes a hollow body delimiting an inner passage for inserting a medical material, the inner passage extending between a proximal opening and a distal opening of the hollow body, a distal seal arranged at the distal opening, a proximal seal arranged at the proximal opening, a spacer element arranged between the distal seal and the proximal seal, and an end cap. The distal seal is an elastic valve that is sealed when idle. The end cap has a fixing element engaging a support element of the hollow body to fix a stacked assembly including the distal seal, the spacer element, and the proximal seal inside the hollow body.

BRIEF DESCRIPTION OF THE DRAWINGS

The invention will now be described by way of example with reference to the accompanying Figures, of which:

FIG. 4 is a schematic sectional perspective view of a distal seal of the hemostasis valve assembly of FIG. 1;

FIG. 5 is another schematic sectional perspective view of the distal seal;

FIG. 6 is a schematic perspective view of the distal seal;

FIG. 7 is another schematic perspective view of the distal seal;

DETAILED DESCRIPTION OF THE EMBODIMENT(S)

The accompanying drawings are incorporated into the specification and form a part of the specification to illustrate several embodiments of the present invention. These drawings, together with the description, serve to explain the principles of the invention. The drawings are merely for the purpose of illustrating examples of how the invention can be made and used, and are not to be construed as limiting the invention to only the illustrated and described embodiments. Furthermore, several aspects of the embodiments may form—individually or in different combinations—solutions according to the present invention. The following described embodiments thus can be considered either alone or in an arbitrary combination thereof. Further features and advantages will become apparent from the following more particular description of the various embodiments of the invention, as illustrated in the accompanying drawings, in which like references refer to like elements.

Figure 1:
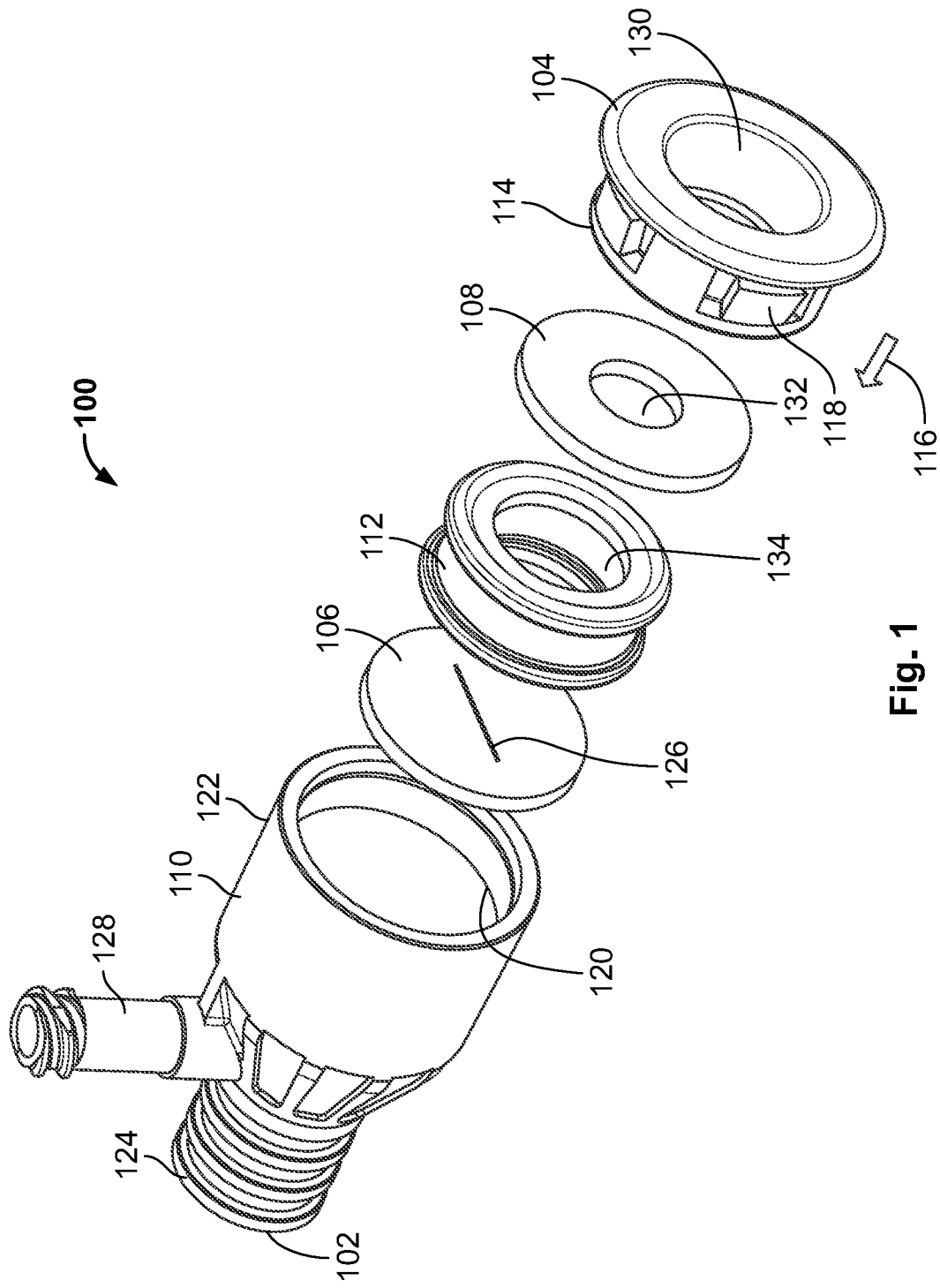
FIG. 1 is an exploded perspective view of a hemostasis valve assembly according to an embodiment.

A hemostasis valve assembly 100 according to an embodiment is shown in FIG. 1. The hemostasis valve assembly 100 has a distal end 102 with a distal opening and a proximal end 104 with a proximal opening. As used herein, the terms "proximal" and "distal" are to be taken as relative to a user using the disclosed delivery devices. "Proximal" is to be understood as relatively closer to the user and "distal" is to be understood as relatively farther away from the user.

The hemostasis valve assembly 100 comprises a distal seal 106 and a proximal seal 108, as shown in FIG. 1. A spacer element 112 separates the distal seal 106 and the proximal seal 108 from each other. The hemostasis valve assembly 100 further comprises a hollow body 110 which encompasses the stacked arrangement formed by the two seals 106, 108 and the spacer element 112. The hollow body 110 has an essentially tubular element 122 delimiting an inner passage for inserting material, such as catheters.

According to the present disclosure, the hemostasis valve assembly 100 is adapted to accommodate medical material (not shown in the Figures) having quite different radial expanses, for example, between 1 mm and 11.3 mm (3 Fr and 34 Fr), by using appropriate dimensions of the two seals 106, 108 and the spacer element 112. The outer dimensions of the hollow body 110, which is also called "hub" in the following, remain the same for all catheter sizes. At the distal end 102, the hollow body 110 has a connector 124 to be connected to a vascular catheter (not shown in the drawings) for insertion into a patient.

In an embodiment, the hollow body 110 may comprise one or more tapping ports 128, as shown in FIG. 1. The tapping port 128 may be used to extract bodily fluids or introduce substances into the patient's vessel, or to provide flushing of the inserted medical material. The tapping port 128 is arranged on a distal side of the distal seal 106.

As shown in FIG. 1, a ring shaped end cap 114 is provided which secures the distal seal 106, the spacer element 112, and the proximal seal 108 inside the hollow body 110. For this purpose, the end cap 114 is inserted into the hollow body 110 in a direction as indicated by the arrow 116. The end cap 114 provides a lumen 130 for the passage of the medical material and, in the shown embodiment, has an essentially tubular shape.

The end cap 114 has a fixing element 118 engaging a support element 120 of the hollow body 110 to attach the end cap 114 to the hollow body 110 in a static manner. In the shown embodiment, the fixing element 118 includes at least one snap-fit hook 118 arranged at the end cap 114 for engaging with the support element 120 embodied as a locking shoulder 120 arranged at the hollow body 110. The support element 120 may have at least one corresponding snap-fit recess in which the snap-fit hooks 118 engage. Four snap-fit hooks 118 are distributed evenly around the circumference of the end cap 114. However, it is clear for a person skilled in the art that any number of snap-fit hooks 118 or also a continuous ring can be provided. Other fixing elements, such as press fit, welding, or gluing, may of course also be used. In the shown embodiment, no threaded connection is used to connect the end cap 114 with the hollow body 110. If desired, the fixing element 118 may be attached in a detachable manner, so that the seals 106, 108 and/or the spacer element 112 can be replaced. The end cap 114 is at least partly encompassed by at least a part of the hollow body 110.

A particularly fast, accurately aligned, and reliable connection between the hollow body 110 and the end cap 114 can be achieved when the end cap 114 is mounted at the hollow body 110 in a static manner by a snap-fit connection. Thus the end cap 114 can be inserted into the hollow body 110 in the axial direction 116 without the need of any threaded parts. The axial forces holding together the assembly 100 can be reached and maintained with improved reproducibility compared to threaded connections.

In an embodiment, at least one of the hollow body 110, the spacer 112, and the end cap 114 is manufactured by 3D printing. This technology allows for a cost-effective, customized fabrication which may also use specifically biocompatible materials.

The distal seal 106 is formed as a slit seal as will be explained in more detail with reference to FIGS. 4-7. Two slits 126, 127 are cut into an elastic material, one from each surface, each extending approximately 50% into the thickness of the seal 106. The two slits 126 include an angle of e. g. 90° with each other. Such a seal design allows a particularly safe sealing already around thin inserted material, such as a guide wire, but also accommodates for high diameter material, such as 34 Fr catheters.

The proximal seal 108 shown in FIG. 1 is formed as a planar elastic ring with a central or inner opening 132. The inner opening 132 delimits a through passage aperture for receiving the medical material therethrough. The opening 132 can be chosen to match the catheter's outer diameter so as to seal and support the catheter during operation.

The modular set up shown in FIG. 1 has the advantage that the parts used for the finally assembled product can be chosen to match a wide range of outer diameters of medical material. In particular, the lumen 130 of the end cap 114, the diameter of the opening 132 of the proximal seal 108, the lumen 134 of the spacer element 112, and (optionally) the length of the slit 126 are adapted to the envisaged catheter dimensions. The hollow body 110, which provides the fluidic connector 124 and defines the outer dimensions of the hemostasis valve assembly 100, may remain the same for all possible catheter sizes. A high design flexibility is achieved and a large range of diameters of medical material can be covered easily at low cost. In an embodiment, the inner opening 132 of the proximal seal 108 has a diameter which is smaller than an inner width of the spacer element 112.

It could be shown that by arranging the ring shaped seal 108 and the slit seal 106 in this sequence, i. e. with the valve functionality of the slit seal 106 at the distal side 102, a safe sealing against the leaking of blood can be achieved, at the same time allowing for an accurate radial guidance and support of the inserted medical material, and for low insertion and retraction forces. According to the present disclosure, the valve function is not actuated by an additional external actuator but by the inserted medical material itself. This greatly simplifies the mechanical set-up of the hemostasis valve assembly 100. Furthermore, the distal seal 106 is capable of returning to a closed position after retraction of the medical material.

Figure 3:
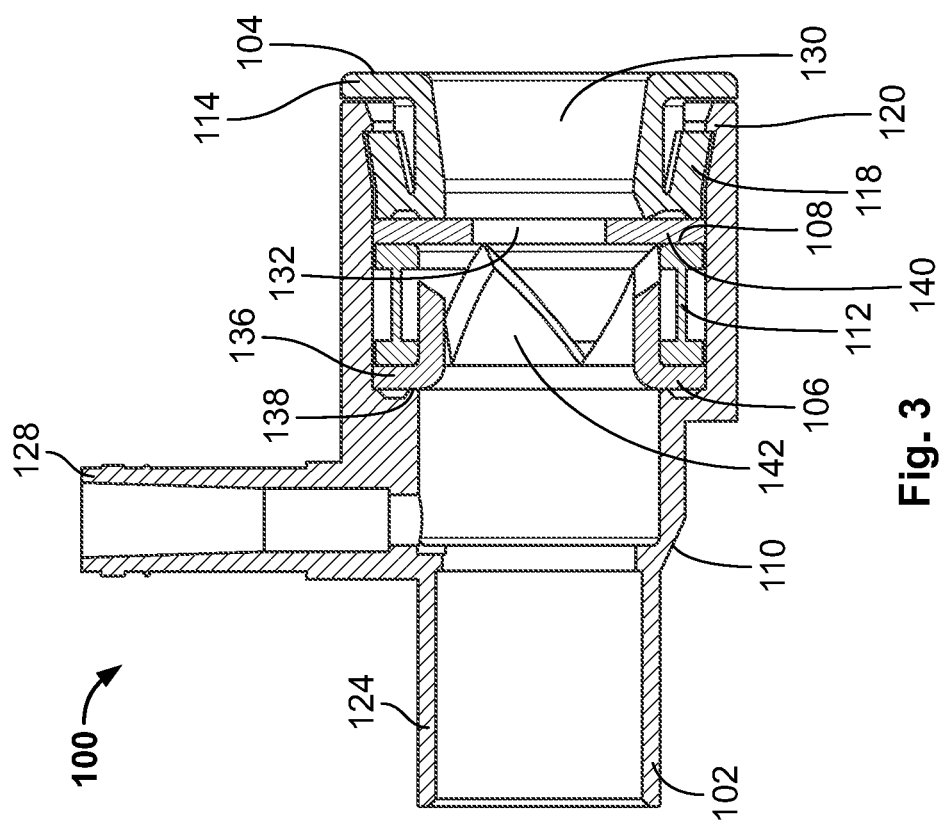
FIG. 3 is a sectional side view of the hemostasis valve assembly of FIG. 1 in a second operational state.
Figure 2:
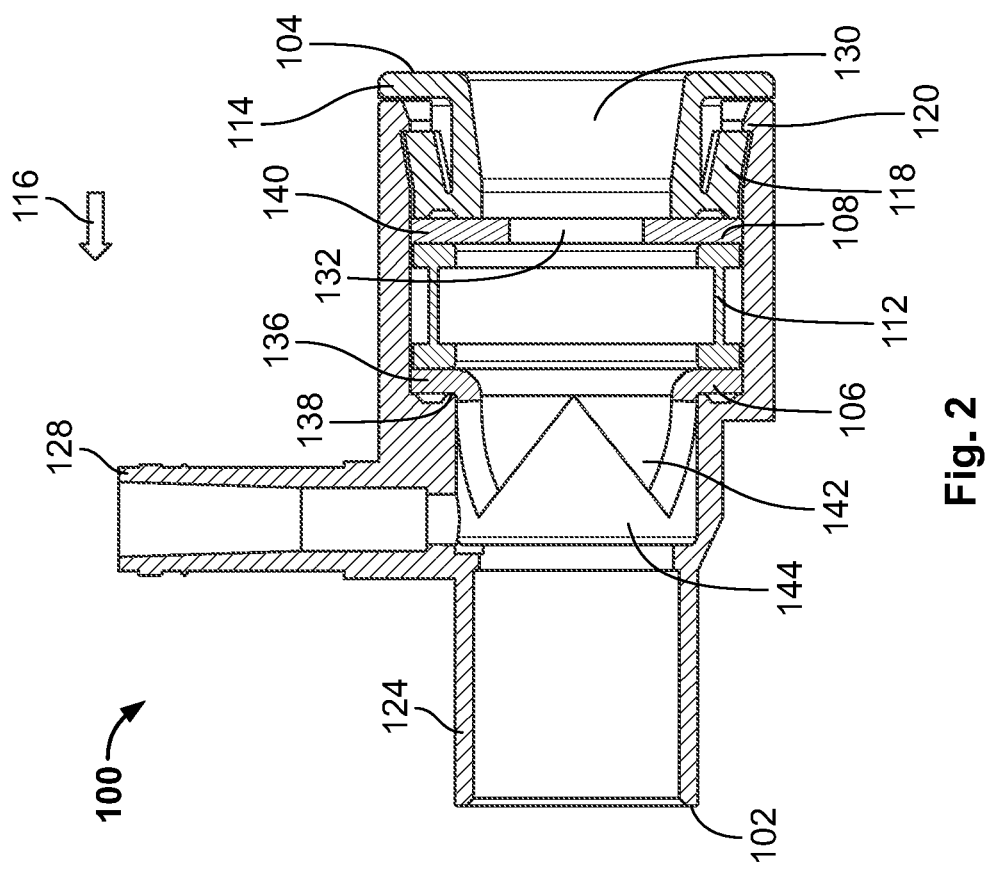
FIG. 2 is a sectional side view of the hemostasis valve assembly of FIG. 1 in a first operational state.

FIGS. 2 and 3 schematically illustrate the deflection of the distal seal 106 during insertion (FIG. 2) and retraction (FIG. 3) of a catheter (not shown in the Figures). As can be seen from these sectional views, the distal seal 106 has a first peripheral region 136 which is compressed between a retaining region 138 at the hollow body 110 and the spacer element 112. The proximal seal 108 has a second peripheral region 140, which is compressed between the spacer element 112 and the end cap 114. The axial compression forces are generated by the locking between the end cap 114 and the hollow body 110. Thus, with one single locking mechanism, a secure clamping and accurate radial and axial alignment of both seals 106, 108 can be achieved.

Turning to FIG. 2, it can be seen that a catheter that was inserted in the direction of arrow 116, displaces four segments 142 of the distal seal 106. The hollow body 110 accommodates the deflected segments 142 within a chamber 144. As will become more apparent from FIGS. 4-7, the segments 142 are formed by at least partly rupturing the areas weakened by the slits 126 when the medical material is inserted. Advantageously, its tearing only happens to such an extent that a safe sealing to the medical material remains intact.

On the other hand, as can be seen in FIG. 3, the spacer element 112 has a recess which provides enough axial space for accommodating the segments 142 during retraction of the catheter in a direction opposite to the insertion direction 116. Advantageously, the distal seal 106 is formed from a resilient material (e. g. silicone) and the segments 142 return into the sealed position after the medical material has been completely retracted. The distal seal 106 and/or the proximal seal 108 are for instance fabricated from an elastic material, such as silicone.

FIGS. 4-7 show several representations of the distal seal 106. When first turning to the sectional view of FIG. 4, the distal seal 106 has a planar disk shape with a circular outline (diameter D) and a thickness X. It is of course clear for a person skilled in the art that any other suitable outline (polygonal, oval, etc.) may also be chosen if necessary to fit the inner cross-sectional outline of the hollow body 110.

According to the present disclosure, incisions, in particular a first radial slit 126 and a second radial slit 127, are cut into the elastic material of the distal seal 106. The first radial slit 126 is cut from a first surface 146 of the distal seal 106 to approximately X/2 (or slightly deeper). The second slit 127 is cut from a second surface 148 of the distal seal 106 opposite the first surface 126 to approximately X/2 (or slightly deeper). The first slit 126 and the second slit 127, in an embodiment, intersect in a center of the distal seal 106 at a radial angle with respect to each other. In the shown embodiment, the radial angle is approximately 90°. Other angles are of course also possible, but an angle of 90° leads to a particularly symmetric force distribution exerted on the inserted medical material. FIGS. 5-7 show further representations of the distal seal 106.

Figure 8:
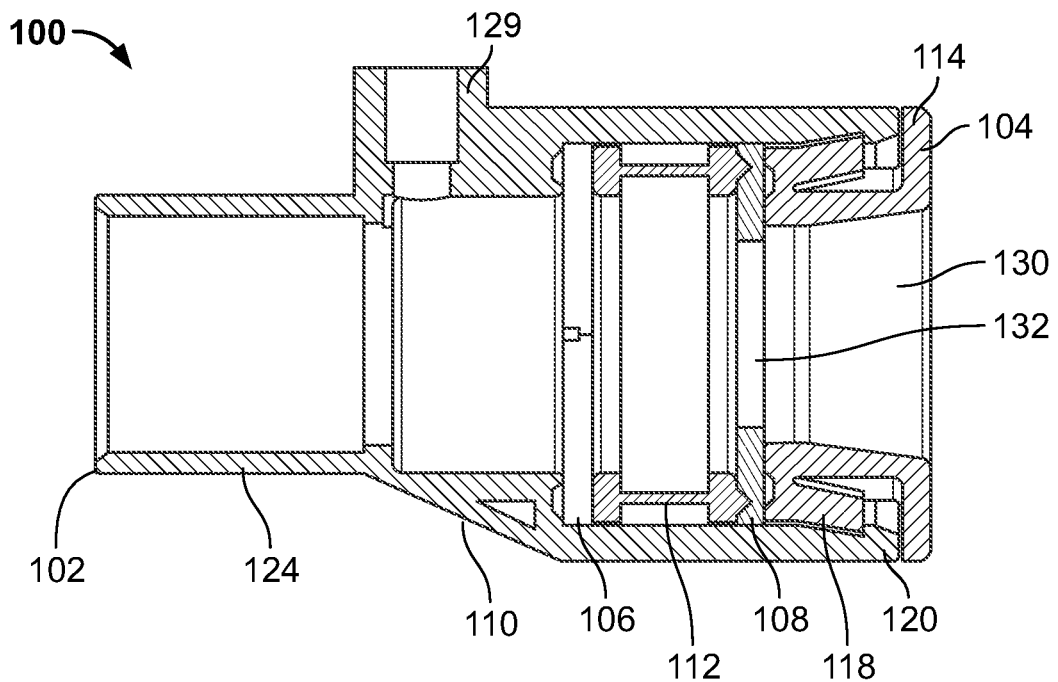
FIG. 8 is a sectional side view of a hemostasis valve assembly according to another embodiment.

According to the present invention, before the first use, the distal seal 106 only has a very small central opening at the intersection of the two incisions 126, 127, which is shut when idle, as shown in FIG. 8. Thus, when a thin guide wire is inserted as the first medical material during use, a tight sealing fit can be achieved around the guide wire. Only when medical material with larger diameters is inserted, the seal 106 partly ruptures along the weakened regions underlying each slit 126, 127, allowing the passage of the medical material, but still providing a tight sealing fit around the outer surface of the medical material. The distal seal 106 may be a part common to all sizes of medical material to be inserted, or may also have optimized slit 126, 127 lengths and geometries to suit specific requirements e. g. of a catheter.

Furthermore, in the embodiment shown in FIG. 8, a tapping port 129 may also be configured as a flush port for bonded flush tube assemblies instead of the Luer screwed connector configuration shown in FIGS. 1-3.

The present invention further relates to a corresponding assembly method. In particular, a method for assembling the hemostasis valve assembly 100 comprises the following steps:

providing the hollow body 110 delimiting an inner passage for inserting a medical material extending between a proximal opening and a distal opening of the hollow body 110, in an axial direction 116, inserting a distal seal 106 to be arranged at the distal opening of the hollow body 110, the distal seal 106 comprising an elastic valve, which is sealed when idle, inserting a spacer element 112 to be in contact with the distal seal 106, inserting a proximal seal 108 to be arranged at the proximal opening of the hollow body 110, so that the spacer element 112 is arranged between the distal seal 106 and the proximal seal 108, mounting an end cap 114, wherein the end cap 114 has a fixing element 118 engaging with a support element 120 provided at the hollow body 110, so that the stacked assembly comprising the distal seal 106, the spacer 112, and the proximal seal 108 is fixed inside the hollow body 110.

Figure 9:
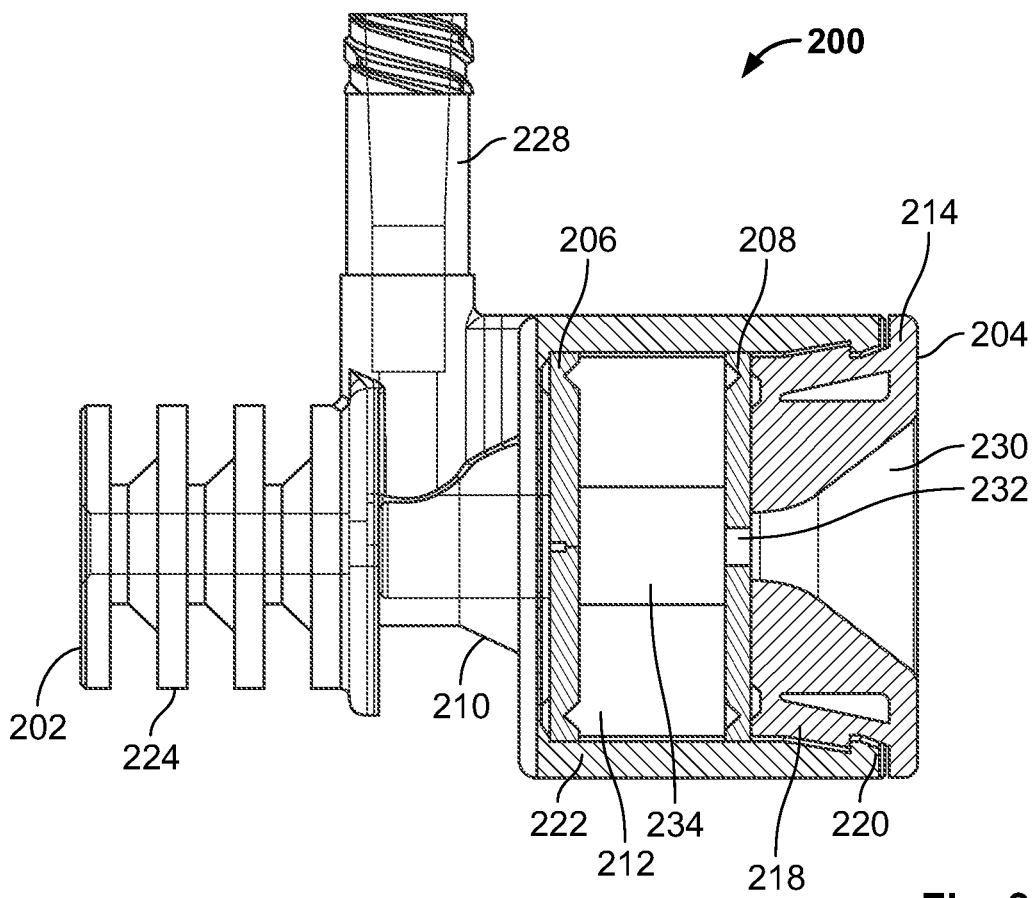
FIG. 9 is a sectional side view of a hemostasis valve assembly according to another embodiment.

A hemostasis valve assembly 200 according to another embodiment is shown in FIG. 9. Like reference numbers refer to like elements and primarily the differences with respect to the hemostasis valve assembly 100 will be described herein.

The valve assembly 200 is particularly adapted to receive and guide small diameter catheters. Consequently, the spacer element 212 has a smaller lumen 234 than the lumen 134 described above. Moreover, the end cap 214 has a funnel shaped lumen 230 which facilitates feeding in very fragile catheters with small diameters. The proximal seal 208 has a reduced diameter opening 232 which is small enough to seal the catheter once it is introduced into the hemostasis valve assembly 200.

The distal seal 206 is shown in the idle closed position in FIG. 9. The distal seal 206 may be formed identical as the seals 106 explained above, or may be adapted regarding the length and depth of the incisions to the smaller diameter medical material that is inserted therethrough. Apart from the smaller diameter of the openings, all other components have analogous functionality as explained above for the hemostasis valve assembly 100 according to the first embodiment.

The present disclosure effectively solves the problem of sealing large diameter 17 Fr+ catheters from blood loss during procedures. The internal construction is improved to allow smooth and low force insertion and withdrawal of the device catheter.

The hemostasis valve assembly 100, 200 according to the present embodiments has a consistent outer profile but can be adapted to have a wide range of inner profiles, further having a high degree of safety during use, at the same time being robust and economic to manufacture.

Each individual part of the hemostasis valve assembly 100, 200 can be fabricated separately, taking advantage of the cost-effectiveness of standardized large-scale production. Moreover, different materials can be used for the fabrication of the body 110, 210, spacer element 112, 212, and seals 106, 108, 206, 208 without the need of complex technologies, e. g. multi-material injection molding. Finally, low insertion and retraction forces can be achieved, which is advantageous for sensitive medical material.

What is claimed is:
1. A hemostasis valve assembly, comprising:
a hollow body delimiting an inner passage for inserting a medical material, the inner passage extending between a proximal opening and a distal opening of the hollow body;
a distal seal arranged at the distal opening, the distal seal is an elastic valve that is sealed when idle;
a proximal seal arranged at the proximal opening, the proximal seal comprising a planar elastic ring having an inner opening delimiting a through passage aperture for receiving the medical material;
a spacer element arranged between the distal seal and the proximal seal, the inner opening of the proximal seal has a diameter smaller than an inner width of the spacer element; and
an end cap having a fixing element engaging a support element of the hollow body to fix a stacked assembly including the distal seal, the spacer element, and the proximal seal inside the hollow body.
2. The hemostasis valve assembly of claim 1, wherein the fixing element is attached to the support element in a static manner.

3. The hemostasis valve assembly of claim 2, wherein the fixing element has a snap-fit hook and the support element has a snap-fit recess into which the snap-fit hook engages.

4. The hemostasis valve assembly of claim 1, wherein the distal seal is an elastic planar seal with a first radial slit and a second radial slit.

5. The hemostasis valve assembly of claim 4, wherein the first radial slit extends from a first surface of the distal seal through approximately half of a total axial thickness of the distal seal and the second radial slit extends from a second surface of the distal seal through approximately half of the total axial thickness of the distal seal.

6. The hemostasis valve assembly of claim 5, wherein the first radial slit and the second radial slit are arranged at a radial angle with respect to each other.

7. The hemostasis valve assembly of claim 6, wherein the first radial slit and the second radial slit are orthogonal to each other.

8. The hemostasis valve assembly of claim 1, wherein the hollow body has a tapping port arranged on a distal side of the distal seal.

9. The hemostasis valve assembly of claim 1, wherein the end cap has an essentially tubular shape and is at least partly encompassed by at least a part of the hollow body.

10. The hemostasis valve assembly of claim 1, wherein the distal seal has a first peripheral region compressed between a retaining region at the hollow body and the spacer element.

11. The hemostasis valve assembly of claim 10, wherein the proximal seal has a second peripheral region compressed between the spacer element and the end cap.

12. The hemostasis valve assembly of claim 11, wherein axial compression forces on the distal seal and the proximal seal are generated by fixing the end cap and the hollow body.

13. A method for assembling a hemostasis valve assembly, comprising:
providing a hollow body delimiting an inner passage for inserting a medical material, the inner passage extending between a proximal opening and a distal opening of the hollow body;
inserting a distal seal in an axial direction into the hollow body, the distal seal arranged at the distal opening of the hollow body, the distal seal is an elastic valve that is sealed when idle;
inserting a spacer element into the hollow body and into contact with the distal seal;
inserting a proximal seal into the hollow body, the proximal seal arranged at the proximal opening of the hollow body, the proximal seal comprising a planar elastic ring having an inner opening delimiting a through passage aperture for receiving the medical material, the inner opening having a diameter smaller than an inner width of the spacer element, the spacer element is arranged between the distal seal and the proximal seal; and
mounting an end cap, the end cap has a fixing element engaging a support element of the hollow body and fixing a stacked assembly including the distal seal, the spacer element, and the proximal seal inside the hollow body.

14. The method of claim 13, wherein at least one of the hollow body, the spacer element, and the end cap is manufactured by 3D printing.

15. The method of claim 13, wherein the end cap is mounted at the hollow body in a static manner by a snap-fit connection.

16. The method of claim 13, wherein the distal seal and the proximal seal are fabricated from an elastic material.

17. The method of claim 16, wherein, during the mounting step, a first peripheral region of the distal seal is compressed between a retaining region at the hollow body and the spacer element.

18. The method of claim 17, wherein, during the mounting step, a second peripheral region of the proximal seal is compressed between the spacer element and the end cap, and axial compression forces are maintained by the fixing of the end cap to the hollow body.

* * * * *